United States Patent [19]

Suh et al.

[11] 4,192,805

[45] Mar. 11, 1980

[54] PROCESS OF PREPARING AMINO ETHANOLS

[75] Inventors: John T. Suh, Mequon, Wis.; Thomas M. Bare, West Chester, Pa.

[73] Assignee: Nicholas International Limited, Melbourne, Australia

[21] Appl. No.: 940,710

[22] Filed: Sep. 8, 1978

Related U.S. Application Data

[63] Continuation of Ser. No. 744,233, Nov. 23, 1976, abandoned.

[30] Foreign Application Priority Data

Nov. 27, 1975 [GB] United Kingdom .............. 48710/75

[51] Int. Cl.$^2$ .......................................... C07D 317/44
[52] U.S. Cl. ............................................. 260/340.5 R
[58] Field of Search ................................ 260/340.5R

[56] References Cited

U.S. PATENT DOCUMENTS

| | | | |
|---|---|---|---|
| 3,135,797 | 6/1964 | Biel | 260/340.5 X |
| 3,657,244 | 4/1972 | Mentrup et al. | 260/340.5 R |
| 3,700,692 | 10/1972 | Suh et al. | 260/340.5 R |
| 3,883,560 | 5/1975 | Suh et al. | 260/340.5 |

OTHER PUBLICATIONS

Cram et al., Organic Chemistry, 2nd Edition, 1964, McGraw-Hill Book Co., pp. 300 and 559.
Theilheimer, Synthetic Methods of Organic Chemistry, vol. 26, Yearbook 1972, S. Karger, pp. 26–13.

*Primary Examiner*—Ethel G. Love
*Attorney, Agent, or Firm*—Foster York

[57] ABSTRACT

The compounds 2-N-[1,1-hydrogen or $C_1$–$C_4$-alkyl-2(3,4-methylenedioxyphenyl)ethyl]amino-1-(3-alkoxycarbonyl or hydroxymethyl-4-benzyloxyphenyl) ethanol compounds, and the process of making these compounds. There is also disclosed a process of making the compounds 2-N-[1,1-hydrogen or $C_1$–$C_4$-alkyl-2(3,4-methylenedioxyphenyl)ethyl]amino-1-(3-hydroxy-4-hydroxy)ethanol.

2 Claims, No Drawings

PROCESS OF PREPARING AMINO ETHANOLS

This is a continuation of application Ser. No. 744,233, filed Nov. 23, 1976, now abandoned.

The present invention relates to an improved process for the preparation of certain aminoethanols useful as bronchodilators and provides intermediates and process steps of said improved process.

U.S. Pat. Nos. 3,700,692 and 3,786,154 and U.K. Pat. No. 1,358,005 claim certain aminoethanols of the formula I

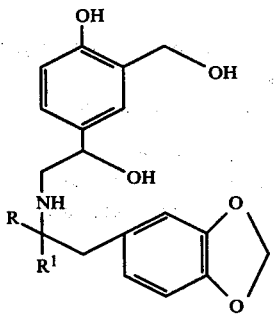
(I)

wherein R and $R^1$ each independently represent hydrogen or a $C_1$–$C_4$ alkyl group. The compounds of formula I can exist in the form of acid addition salts; for example they can be in the form of their nitrate, sulphate or hydrochloride. The compounds of formula I have been found in preliminary screening tests to be orally effective bronchodilators which produce a more potent and sustained bronchodilation than isoproterenol while having less undesirable side effects on the contractile forces and heart rates of test animals than does isoproterenol.

We have now discovered an improved process for preparing the compounds of formula I which comprises reacting a compound of formula IIA

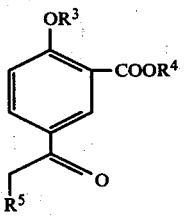
(IIA)

(wherein $R^3$ represents a protecting group for an aromatic hydroxyl function; $R^4$ represents an alkyl group, e.g., a methyl group, ethyl group, n-propyl group, isopropyl or a butyl group; and $R^5$ represents a halogen atom) in an appropriate solvent with a compound of formula IIB

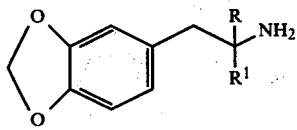
(IIB)

(wherein R and $R^1$ have the meanings previously given) to give a compound of formula III

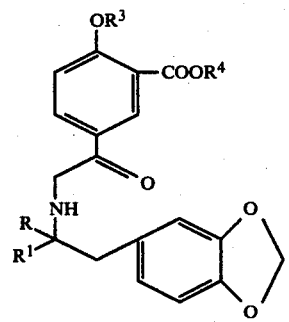
(III)

(wherein R, $R^1$, $R^3$ and $R^4$ have the meanings previously given), reducing the compound of formula III to obtain a compound of formula IV

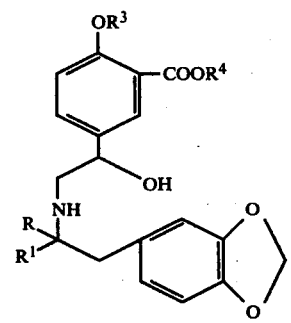
(IV)

(wherein R, $R^1$, $R^3$ and $R^4$ have the meanings previously defined); reducing the compound of formula IV to give a compound of formula V

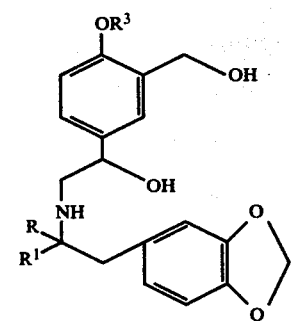
(V)

(wherein R, $R^1$ and $R^3$ have the meanings previously given); removing the protecting group $R^3$ to give a compound of formula I, and if desired converting the compound of formula I to a salt by reaction with an appropriate acid.

The reaction between the compound of formula IIA and the compound of formula IIB can conveniently be carried out in an inert polar solvent such as tetrahydrofuran. When the group $R^4$ in the product of formula IV is a methyl group it is preferably converted into a branched chain alkyl group such as an isopropyl group which is more readily reactable with a metal hydride. The conversion can be carried out by refluxing the compound of formula IV in the appropriate alcohol in the presence of an alkali metal borohydride such as sodium borohydride. The compound of formula IV is then reduced to the compound of formula V by metal hydride reduction (see H. O. House, Modern Synthetic Reactions, W. A. Benjamin Inc. 1965 at Chapter 2) after which the resulting mixture is treated with water and the compound of formula V is isolated. The protecting group $R^3$ is then removed by conventional means, for example when (as is preferred) $R^3$ is a benzyl group by catalytic hydrogenation using palladium on charcoal, after which the resulting compound of formula I can if desired be converted into an acid addition salt by treatment with an acid, for example sulphuric acid, hydrochloric acid or nitric acid.

The following compounds of formula I can be prepared by the novel process described above:

2-N-[1,1-dimethyl-2-(3,4-methylenedioxyphenyl)ethyl]-1-(3-hydroxymethyl-4-hydroxyphenyl)aminoethanol, otherwise referred to as $\alpha^1$-[[($\alpha,\alpha$-dimethyl-3,4-methylenedioxyphenethyl)amino]methyl]-4-hydroxy-m-xylene-$\alpha^1,\alpha^3$-diol;

2-N-[2-(3,4-methylenedioxyphenyl)ethyl]-1-(3-hydroxymethyl-4-hydroxyphenyl)aminoethanol, otherwise referred to as $\alpha^1$-[[(3,4-methylenedioxyphenethyl)amino]methyl]-4-hydroxy-m-xylene-$\alpha^1,\alpha^3$-diol;

2-N-[1-ethyl-2-(3,4-methylenedioxyphenyl)ethyl]-1-(3-hydroxymethyl-4-hydroxyphenyl)aminoethanol, otherwise referred to as $\alpha^1$-[[($\alpha$-ethyl-3,4-methylenedioxyphenethyl)amino]methyl]-4-hydroxy-m-xylene-$\alpha^1,\alpha^3$-diol;

2-N-[1-isopropyl-2-(3,4-methylenedioxyphenyl)ethyl]-1-(3-hydroxymethyl-4-hydroxyphenyl)aminoethanol, otherwise referred to as $\alpha^1$-[[($\alpha$-isopropyl-3,4-methylenedioxyphenethyl)amino]methyl]-4-hydroxy-m-xylene-$\alpha^1,\alpha^3$-diol; and 2-N-[1-methyl-2-(3,4-methylenedioxyphenyl)ethyl]-1-(3-hydroxymethyl-4-hydroxyphenyl)aminoethanol, otherwise referred to as $\alpha^1$-[[($\alpha$-methyl-3,4-methylenedioxyphenethyl)amino]methyl]-4-hydroxy-m-xylene-$\alpha^1,\alpha^3$-diol.

The said process has the advantage that it involves less processing steps and hence is more economic than the processes described in U.S. Pat. Nos. 3,700,692 and 3,786,154 and U.K. Pat. No. 1,358,005 and also that it avoids the chloromethylation steps used in the said processes which may be hazardous to carry out.

According to one aspect of the present invention, there is provided compounds having the formula IV

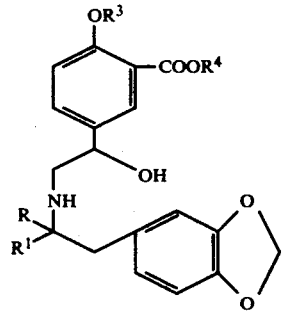

wherein

R and $R^1$ independently represent hydrogen or a $C_1$–$C_4$ alkyl group, $R^3$ represents a protecting group for an aromatic hydroxyl function and $R^4$ represents an alkyl group.

The invention also provides a process for preparing a compound of formula IV which comprises reducing a compound of formula III

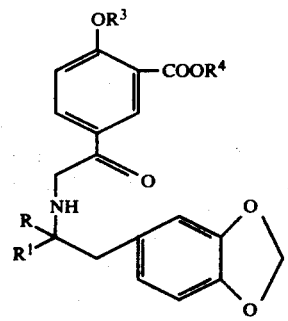

wherein

R and $R^1$ independently represent hydrogen or a $C_1$–$C_4$ alkyl group $R^3$ represents a protecting group for an aromatic hydroxyl function and $R^4$ represents an alkyl group.

The compounds of formula III can be prepared as described previously, i.e. by reacting a compound of formula IIA

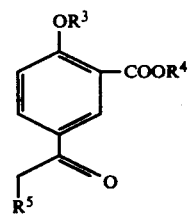

wherein $R^3$ represents a protecting group for an aromatic hydroxyl function, $R^4$ represents an alkyl group and $R^5$ represents a halogen atom with a compound of formula IIB

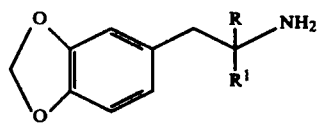

wherein R and $R^1$ independently represent hydrogen or a $C_1$–$C_4$ alkyl group.

The invention further provides a process for preparing a compound of formula V

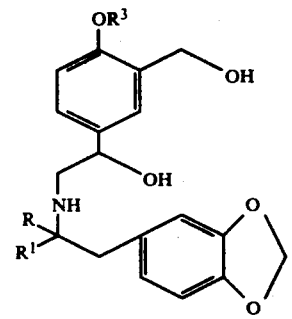

wherein

R and $R^1$ independently represent hydrogen or a $C_1$-$C_4$ alkyl group, and $R^3$ represents a protecting group for an aromatic hydroxyl function,
which comprises reducing a compound of formula IV.

The compounds of formula V can as described previously, be converted into compounds of formula I by removing the hydroxyl protecting group $R^3$.

The compounds of formula I in which R and $R^1$ are different exist as diastereomeric isomers. The described method of preparing the compounds of formula I results in a mixture of two isomers having different melting points. The high melting isomer may be isolated from the low melting isomer in a substantially pure form by forming the nitrate salts of the two isomers and selectively precipitating the nitrate salts from a solvent such as anhydrous ether. The high melting isomer precipitates first and can be purified, if desired, by recrystallization from a suitable solvent such as 2-propanol. In the case of the compound 2-N-[1-methyl-2-(3,4-methylenedioxyphenyl)ethyl]-1-(3-hydroxymethyl-4-hydroxyphenyl)aminoethanol, the purified high melting isomer is a white solid which has a melting point of about 127°–135° C.

Both of the diastereoisomers, as well as the mixture of the isomers of the compounds of formula I are orally effective as bronchodilators and produce a more potent and sustained bronchodilation than isoproterenol. Furthermore, both isomers have less undesirable side effects on the contractile forces and heart rate of test animals than does isoproterenol.

Pharmaceutical compositions will generally contain the compounds of formula I as a mixture of any diastereoisomers or optical isomers. Such compositions may take the form of tablets, capsules, solutions or suspensions for oral administration or solutions for inhalation or parenteral administration. The active ingredients are generally employed in the form of their free bases. However, they may be employed in the form of their acid addition salts such as the nitrates, the hydrochlorides, the sulfates and the like. In addition to the active ingredients, the compositions will usually contain conventional pharmaceutical diluents and excipients.

The individual dosage forms may contain from about 0.02 mg or less of the active ingredient calculated as the free base to more than 10 mg. Generally, the daily dose will be equivalent in terms of the free base to an intraperitoneal dose of from about 2 mg/kg to about 200 mg/kg of body weight.

The invention is illustrated in the following Example:

EXAMPLE

Preparation of 2-N-[1,1-dimethyl-2-(3,4-methylenedioxyphenyl)ethyl]-1-(3-hydroxymethyl-4-hydroxyphenyl) aminoethanol (a)

N-[1,1-Dimethyl-2-(3,4-methylenedioxyphenyl)ethyl]aminomethyl 3-methoxycarbonyl-4-benzyloxyphenyl ketone A solution of 11.8 g (0.061 mole) of 1,1-dimethyl-2-(3,4-methylenedioxyphenyl)ethylamine in 151 ml of tetrahydrofuran was treated with 11.1 g (0.0306 mole) of methyl 2-benzyloxy-5-bromoacetylbenzoate. The resulting solution was stirred for 5.5 hours and allowed to stand for a further 48 hours after which it was cooled, the solid which had separated was filtered off and the filtrate was concentrated by evaporation. The filtered solid and the filtrate were then recombined and the mixture was covered with 100 ml of methanol, warmed to 35°, stirred at that temperature for 30 minutes and cooled. A solid which separated was filtered off, washed with methanol and air dried to give N-[1,1-dimethyl-2-(3,4-methylenedioxyphenyl)ethyl]aminomethyl 3-methoxycarbonyl-4-benzyloxyphenyl ketone as a white solid, m.p. 134°–141° C. (Yield 10.48 g, 72.0%).

(b)

2-N-[1,1-Dimethyl-2-(3,4-methylenedioxyphenyl)ethyl]amino-1-(3-isopropoxycarbonyl-4-benzyloxyphenyl)ethanol A mixture of 9.9 g (0.0208 mole) of N-[1,1-dimethyl-2-(3,4-methylenedioxyphenyl)ethyl]aminomethyl 3-methoxy-carbonyl-4-benzyloxyphenyl ketone and 0.79 g (0.0208 mole) of sodium borohydride in 99 ml of 2-propanol was heated to the reflux temperature over a period of 25 minutes after which it was refluxed for 15 minutes. The solution was cooled slightly and concentrated to a viscous oil. Water (150 ml) was added and the mixture was heated to the reflux temperature over a period of 15 minutes and refluxed for 10 minutes. The mixture was then cooled to room temperature, seeded, and allowed to stand at room temperature overnight, during which time it solidified. The solid was washed with water and dried to give crude 2-N-[1,1-dimethyl-2-(3,4-methylenedioxyphenyl)ethyl]amino-1-(3-isopropoxycarbonyl-4-benzyloxyphenyl)ethanol as a white solid m.p. 98°–102° which was recrystallized from 30 ml of 2-propanol to give the pure product as a white solid m.p. 102°–104° (Yield 2.2 g, 78.0%).

(c)

2-N-[1,1-Dimethyl-2-(3,4-methylenedioxyphenyl)ethyl]amino-1-(3-hydroxymethyl-4-benzyloxyphenyl)ethanol A dispersion of 3.3 g (0.087 mole) of lithium aluminium hydride in 500 ml of ether was treated with 22.0 g (0.44 mole) of 2-N-[1,1-dimethyl-2-(3,4-methylenedioxyphenyl)ethyl]amino-1-(3-isopropoxycarbonyl-4-benzyloxyphenyl)ethanol over a period of 5 minutes after which the mixture was refluxed for 2½ hours, allowed to stand at room temperature for 48 hours, and then refluxed for a further 1½ hours. The mixture was then cooled and the complex present was decomposed by successive addition of 3.3 ml of water, 3.3 ml of a 20% aqueous solution of sodium hydroxide and then a further 9.9 ml of water, after which the mixture was refluxed for 30 minutes and cooled. The solid which separated was filtered off and the filtrate was concentrated to yield a semi-solid product which was crystallised from 150 ml of hot toluene to give 2-N-[1,1-dimethyl-2-(3,4-methylenedioxyphenyl)ethyl]amino-1-(3-hydroxymethyl-4-benzyloxyphenyl)ethanol as a white solid m.p. 66°–70° C. (Yield 78.1 g, 92.6%).

(d)

2-N-[1,1-Dimethyl-2-(3,4-methylenedioxyphenyl)ethyl]-1-(3-hydroxymethyl-4-hydroxyphenyl)aminoethanol 6.85 g (0.0152 mole) of 2-N-[1,1-dimethyl-2-(3,4-methylenedioxyphenyl)ethyl]amino-1-(3-hydroxymethyl-4-benzyloxyphenyl)ethanol was hydrogenated at atmospheric pressure in 65 ml of S.D.A.-30 as solvent in the presence of 1.8 g of palladium on carbon. After 90 minutes the theoretical volume of hydrogen had been taken up, after which hydrogen uptake ceased. The mixture was filtered, and the filtrate was concentrated by evaporation to give a gum which was dissolved in 30 ml of ethyl acetate and cooled. The white solid which precipitated was separated off and recrystallised from ethyl acetate to give 2-N-[1,1-dimethyl-2-(3,4-methylenedioxyphenyl)ethyl]-1-(3-hydroxymethyl-4-hydroxyphenyl)aminoethanol as a white solid m.p. 118.5°–119.5° C.

ANALYSIS: Calculated for $C_{20}H_{25}NO_5$: C, 66.83%; H, 7.01%; N, 3.90%. Found: C, 66.83%; H, 7.03%; N, 3.88%.

We claim:

1. A process of preparing a compound of the formula

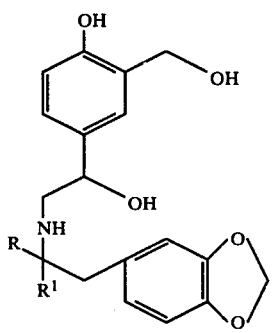

wherein R and $R^1$ each independently represent hydrogen or a $C_1$–$C_4$ alkyl group, which comprises (1) reacting a compound of the formula

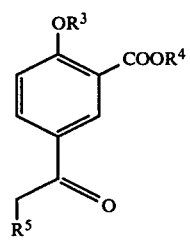

wherein $R^3$ represents a benzyl protecting group, $R^4$ represents an alkyl group, and $R^5$ represents a halogen atom in a solvent with a compound of formula

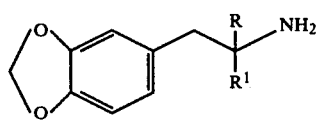

wherein R and $R^1$ have the meanings given above, to give a compound of formula

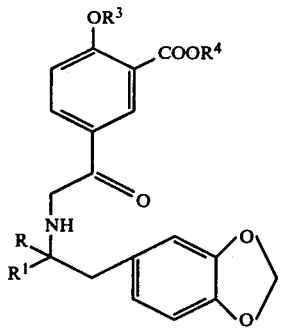

wherein R, $R^1$, $R^3$ and $R^4$ have the meanings given above, (2) reducing said latter compound with an alkali metal borohydride to obtain a compound of formula

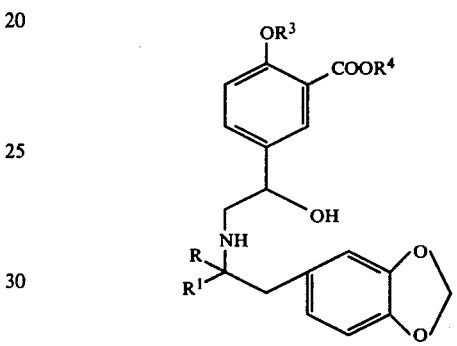

wherein R, $R^1$, $R^3$ and $R^4$ have the meanings given above, (3) reducing said latter compound with a metal hydride to give a compound of formula

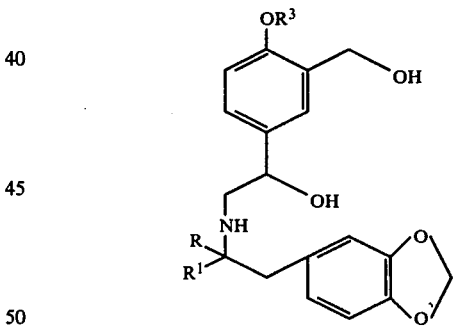

wherein R, $R^1$ and $R^3$ have the meanings given above, and (4) removing the protecting benzyl group by hydrogenation in the presence of a hydrogenation catalyst.

2. The process of claim 1 wherein the reduction in step 2 is carried out with sodium borohydride, the reduction in step 3 is carried out with lithium aluminum hydride, and the removal of the benzyl group in step 4 is carried out by hydrogenation in the presence of a hydrogenation catalyst.

* * * * *